(12) United States Patent
Spratt et al.

(10) Patent No.: US 8,430,914 B2
(45) Date of Patent: Apr. 30, 2013

(54) ASSEMBLY FOR ORTHOPAEDIC SURGERY

(75) Inventors: Frank Spratt, Bole (CH); Martin Pfleiderer, Auvernier (CH)

(73) Assignee: DePuy Spine, Inc., Raynham, MA (US)

( * ) Notice: Subject to any disclaimer, the term of this patent is extended or adjusted under 35 U.S.C. 154(b) by 561 days.

(21) Appl. No.: 12/257,404

(22) Filed: Oct. 24, 2008

(65) Prior Publication Data

US 2009/0198280 A1    Aug. 6, 2009

(30) Foreign Application Priority Data

Oct. 24, 2007  (GB) ................................ 0720762.4

(51) Int. Cl.
*A61B 17/70* (2006.01)
(52) U.S. Cl.
USPC ............ 606/265; 606/268; 606/269; 606/266
(58) Field of Classification Search .......... 606/250–270, 606/271–278, 279, 246–249; 403/348–349; 411/396
See application file for complete search history.

(56) References Cited

U.S. PATENT DOCUMENTS

| | | | |
|---|---|---|---|
| 2,669,896 A | 2/1954 | Clough | |
| 2,952,285 A | 9/1960 | Roosli | |
| 3,604,487 A | 9/1971 | Gilbert | |
| 3,786,806 A | 1/1974 | Johnson et al. | |
| 3,915,160 A | 10/1975 | Lode | |
| 4,289,123 A | 9/1981 | Dunn | |
| 4,363,250 A | 12/1982 | Suga | |
| 4,592,933 A | 6/1986 | Meyerson | |
| 4,611,582 A | 9/1986 | Duff | |
| 4,697,582 A | 10/1987 | William | |
| 4,733,657 A | 3/1988 | Kluger | |
| 4,743,260 A | 5/1988 | Burton | |

(Continued)

FOREIGN PATENT DOCUMENTS

| | | |
|---|---|---|
| DE | 4107480 | 9/1994 |
| DE | 10005386 | 8/2001 |

(Continued)

OTHER PUBLICATIONS

Advanced Energy, Industrial Processes: "Infrared (IR) Heating," "Microwave Heating," Radio Frequency and "Catalytic Heating," (2003).

(Continued)

*Primary Examiner* — Jan Christopher Merene (57) ABSTRACT

An assembly for connecting a support element to a bone. The assembly comprises: a bone screw having a head at one end of a threaded shaft; and a clamp comprising: a base at a first end of the clamp delimiting an opening for receiving the head of the bone screw; and at least two side members extending from the base towards a second end of the clamp. The head of the bone screw and the clamp are configured to allow the head of the bone screw to be inserted into the base from the direction of the first end at a first orientation of the base to the bone screw, and to retain an inserted bone screw within the base at a second orientation of the base relative to the bone screw. This allows the screw to be inserted into the bone without requiring prior assembly of the screw and clamp. It also allows later revision whereby the clamp can be removed from the screw without requiring an implanted screw to be removed from the bone.

14 Claims, 6 Drawing Sheets

U.S. PATENT DOCUMENTS

| | | |
|---|---|---|
| 4,887,596 A | 12/1989 | Sherman |
| 4,957,495 A | 9/1990 | Kluger |
| 4,987,892 A | 1/1991 | Krag |
| 5,005,562 A | 4/1991 | Cotrel |
| 5,042,982 A | 8/1991 | Harms |
| 5,067,955 A | 11/1991 | Cotrel |
| 5,092,866 A | 3/1992 | Breard |
| 5,102,412 A | 4/1992 | Rogozinski |
| 5,120,171 A | 6/1992 | Lasner |
| 5,129,388 A | 7/1992 | Vignaud |
| 5,129,900 A | 7/1992 | Asher |
| 5,133,716 A | 7/1992 | Plaza |
| 5,176,678 A | 1/1993 | Tsou |
| 5,176,680 A | 1/1993 | Vignaud |
| 5,181,917 A | 1/1993 | Rogozinski |
| 5,190,543 A | 3/1993 | Schlapfer |
| 5,207,678 A | 5/1993 | Harms |
| 5,219,349 A | 6/1993 | Krag |
| 5,226,766 A | 7/1993 | Lasner |
| 5,263,939 A | 11/1993 | Wortrich |
| 5,282,801 A | 2/1994 | Sherman |
| 5,282,863 A | 2/1994 | Burton |
| 5,290,289 A | 3/1994 | Sanders |
| 5,312,404 A | 5/1994 | Asher |
| 5,330,473 A | 7/1994 | Howland |
| 5,360,431 A | 11/1994 | Puno |
| 5,385,565 A | 1/1995 | Ray |
| 5,387,212 A | 2/1995 | Yuan |
| 5,387,213 A | 2/1995 | Breard |
| 5,391,168 A | 2/1995 | Sanders |
| 5,413,576 A | 5/1995 | Rivard |
| 5,415,661 A | 5/1995 | Holmes |
| 5,437,669 A | 8/1995 | Yuan |
| 5,437,673 A | 8/1995 | Baust |
| 5,445,140 A | 8/1995 | Tovey |
| 5,466,238 A | 11/1995 | Lin |
| 5,468,241 A | 11/1995 | Metz-Stavenhagen |
| 5,487,742 A | 1/1996 | Cotrel |
| 5,487,744 A | 1/1996 | Howland |
| 5,499,983 A | 3/1996 | Hughes |
| 5,501,684 A | 3/1996 | Schlapfer |
| 5,520,689 A | 5/1996 | Schlapfer |
| 5,536,127 A | 7/1996 | Pennig |
| 5,536,268 A | 7/1996 | Griss |
| 5,540,688 A | 7/1996 | Navas |
| 5,540,689 A | 7/1996 | Sanders |
| 5,545,165 A | 8/1996 | Biedermann |
| 5,549,552 A | 8/1996 | Peters |
| 5,549,608 A | 8/1996 | Errico |
| 5,586,983 A | 12/1996 | Sanders |
| 5,591,166 A | 1/1997 | Bernhardt |
| 5,593,407 A | 1/1997 | Reis |
| 5,593,408 A | 1/1997 | Gayet |
| 5,597,378 A | 1/1997 | Jervis |
| 5,601,552 A | 2/1997 | Cotrel |
| 5,626,581 A | 5/1997 | Staehlin |
| 5,630,816 A | 5/1997 | Kambin |
| 5,645,520 A | 7/1997 | Nakamura |
| 5,649,931 A | 7/1997 | Bryant |
| 5,651,789 A | 7/1997 | Cotrel |
| 5,658,286 A | 8/1997 | Sava |
| 5,667,513 A | 9/1997 | Torrie |
| 5,672,175 A | 9/1997 | Martin |
| 5,672,176 A | 9/1997 | Biedermann |
| 5,702,452 A | 12/1997 | Argenson |
| 5,725,527 A | 3/1998 | Biedermann |
| 5,738,685 A | 4/1998 | Halm |
| 5,743,907 A | 4/1998 | Asher |
| 5,743,911 A | 4/1998 | Cotrel |
| 5,766,004 A | 6/1998 | Besselink |
| 5,797,911 A | 8/1998 | Sherman |
| 5,830,179 A | 11/1998 | Mikus |
| 5,833,707 A | 11/1998 | McIntyre |
| 5,879,350 A | 3/1999 | Sherman |
| 5,882,350 A | 3/1999 | Ralph |
| 5,885,285 A | 3/1999 | Simonson |
| RE36,211 E | 5/1999 | Nonomura |
| 5,899,903 A | 5/1999 | Cotrel |
| 5,910,141 A | 6/1999 | Morrison |
| 5,910,142 A | 6/1999 | Tatar |
| 5,919,158 A | 7/1999 | Saperstein |
| 5,947,965 A | 9/1999 | Bryan |
| 5,947,966 A | 9/1999 | Drewry |
| 5,951,555 A | 9/1999 | Rehak |
| 5,961,515 A | 10/1999 | Taylor |
| 5,964,760 A | 10/1999 | Richelsoph |
| 5,964,770 A | 10/1999 | Flomenblit |
| 5,989,250 A | 11/1999 | Wagner |
| 5,989,254 A | 11/1999 | Katz |
| 5,997,580 A | 12/1999 | Mastrorio |
| 6,050,997 A | 4/2000 | Mullane |
| 6,063,090 A | 5/2000 | Schlapfer |
| 6,071,250 A | 6/2000 | Douglas |
| 6,074,391 A | 6/2000 | Metz-Stavenhagen |
| 6,077,262 A | 6/2000 | Schlapfer |
| 6,090,110 A | 7/2000 | Metz-Stavenhagen |
| 6,090,113 A | 7/2000 | Le Couedic |
| 6,102,912 A | 8/2000 | Cazin |
| 6,106,527 A | 8/2000 | Wu |
| 6,110,172 A | 8/2000 | Jackson |
| 6,127,597 A | 10/2000 | Beyar |
| 6,139,548 A | 10/2000 | Errico |
| 6,139,549 A | 10/2000 | Keller |
| 6,146,383 A | 11/2000 | Studer |
| 6,183,472 B1 | 2/2001 | Lutz |
| 6,200,317 B1 | 3/2001 | Aalsma |
| 6,204,060 B1 | 3/2001 | Mehtali |
| 6,214,006 B1 | 4/2001 | Metz-Stavenhagen |
| 6,214,730 B1 | 4/2001 | Cooney, III |
| 6,235,028 B1 | 5/2001 | Brumfield |
| 6,238,491 B1 | 5/2001 | Davidson |
| 6,241,730 B1 | 6/2001 | Alby |
| 6,254,602 B1 | 7/2001 | Justis |
| 6,261,287 B1 | 7/2001 | Metz-Stavenhagen |
| 6,261,288 B1 | 7/2001 | Jackson |
| 6,267,764 B1 | 7/2001 | Elberg |
| 6,273,914 B1 | 8/2001 | Papas |
| 6,280,442 B1 | 8/2001 | Barker |
| 6,280,443 B1 | 8/2001 | Gu |
| 6,293,949 B1 | 9/2001 | Justis |
| 6,299,216 B1 | 10/2001 | Thompson |
| 6,302,888 B1 | 10/2001 | Mellinger |
| 6,306,141 B1 | 10/2001 | Jervis |
| 6,309,389 B1 | 10/2001 | Baccelli |
| 6,309,391 B1 | 10/2001 | Crandall |
| 6,325,805 B1 | 12/2001 | Ogilvie |
| 6,328,741 B1 | 12/2001 | Richelsoph |
| 6,361,637 B2 | 3/2002 | Martin |
| 6,368,321 B1 | 4/2002 | Jackson |
| 6,379,357 B1 | 4/2002 | Bernstein |
| 6,389,710 B1 | 5/2002 | Chou |
| 6,402,752 B2 | 6/2002 | Schaffler-Wachter |
| 6,423,065 B2 | 7/2002 | Ferree |
| 6,440,133 B1 | 8/2002 | Beale |
| 6,440,137 B1 | 8/2002 | Horvath |
| 6,443,953 B1 | 9/2002 | Perra |
| 6,447,478 B1 | 9/2002 | Maynard |
| 6,471,716 B1 | 10/2002 | Pecukonis |
| 6,478,798 B1 | 11/2002 | Howland |
| 6,485,491 B1 | 11/2002 | Farris |
| 6,485,492 B1 | 11/2002 | Halm |
| 6,517,533 B1 | 2/2003 | Swaminathan |
| 6,520,962 B1 | 2/2003 | Taylor |
| 6,537,276 B2 | 3/2003 | Metz-Stavenhagen |
| 6,540,748 B2 | 4/2003 | Lombardo |
| 6,540,749 B2 | 4/2003 | Schëfer |
| 6,551,320 B2 | 4/2003 | Lieberman |
| 6,554,834 B1 | 4/2003 | Crozet |
| 6,565,567 B1 | 5/2003 | Haider |
| 6,597,279 B1 | 7/2003 | Haraguchi |
| 6,616,669 B2 | 9/2003 | Ogilvie |
| 6,623,485 B2 | 9/2003 | Doubler |
| 6,648,888 B1 | 11/2003 | Shluzas |
| 6,652,526 B1 | 11/2003 | Arafiles |
| 6,660,006 B2 | 12/2003 | Markworth |
| 6,689,137 B2 | 2/2004 | Reed |
| 6,692,500 B2 | 2/2004 | Reed |

| | | |
|---|---|---|
| 6,695,843 B2 | 2/2004 | Biedermann |
| 6,706,044 B2 | 3/2004 | Kuslich |
| 6,716,214 B1 * | 4/2004 | Jackson .................. 606/266 |
| 6,730,087 B1 | 5/2004 | Butsch |
| 6,733,502 B2 | 5/2004 | Altarac |
| 6,733,531 B1 | 5/2004 | Trieu |
| 6,743,231 B1 | 6/2004 | Gray |
| 6,749,613 B1 | 6/2004 | Conchy |
| 6,755,829 B1 | 6/2004 | Bono |
| 6,761,719 B2 | 7/2004 | Justis |
| 6,783,527 B2 | 8/2004 | Drewry |
| 6,786,984 B1 | 9/2004 | Hanada |
| 6,800,078 B2 | 10/2004 | Reed |
| 6,800,079 B2 | 10/2004 | Reed |
| 6,800,778 B1 | 10/2004 | Aoki |
| 6,802,844 B2 | 10/2004 | Ferree |
| 6,837,889 B2 | 1/2005 | Shluzas |
| 6,872,208 B1 | 3/2005 | McBride |
| 6,881,220 B2 | 4/2005 | Edwin |
| 6,887,241 B1 | 5/2005 | McBride |
| 6,964,666 B2 | 11/2005 | Jackson |
| 6,984,242 B2 | 1/2006 | Campbell |
| 6,986,771 B2 | 1/2006 | Paul |
| 6,989,011 B2 | 1/2006 | Paul |
| 7,010,866 B1 | 3/2006 | Lin |
| 7,044,966 B2 | 5/2006 | Svanidze |
| 7,044,982 B2 | 5/2006 | Milbocker |
| 7,063,706 B2 | 6/2006 | Wittenstein |
| 7,066,938 B2 | 6/2006 | Slivka |
| 7,094,237 B2 | 8/2006 | Gradel |
| 7,104,993 B2 | 9/2006 | Baynham |
| 7,125,410 B2 | 10/2006 | Freudiger |
| 7,128,743 B2 | 10/2006 | Metz-Stavenhagen |
| 7,128,758 B2 | 10/2006 | Cox |
| 7,179,261 B2 | 2/2007 | Sicvol |
| 7,207,986 B2 | 4/2007 | Abboud |
| 7,267,687 B2 | 9/2007 | McGuckin, Jr. |
| 7,322,979 B2 | 1/2008 | Crandall |
| 7,335,200 B2 | 2/2008 | Carli |
| 7,377,923 B2 | 5/2008 | Purcell |
| 7,381,625 B2 | 6/2008 | Xi |
| 7,429,042 B2 | 9/2008 | Ban |
| 7,442,192 B2 | 10/2008 | Knowlton |
| 7,455,685 B2 | 11/2008 | Justis |
| 7,459,042 B2 | 12/2008 | Parker |
| 7,465,306 B2 | 12/2008 | Pond, Jr. |
| 7,473,267 B2 | 1/2009 | Nguyen |
| 7,481,827 B2 | 1/2009 | Ryan |
| 7,491,218 B2 | 2/2009 | Landry |
| 7,494,488 B2 | 2/2009 | Weber |
| 7,507,248 B2 | 3/2009 | Beaurain |
| 7,559,942 B2 | 7/2009 | Paul |
| 7,588,575 B2 | 9/2009 | Colleran |
| 7,604,653 B2 | 10/2009 | Kitchen |
| 7,621,912 B2 | 11/2009 | Harms |
| 7,632,292 B2 | 12/2009 | Sengupta |
| 7,635,380 B2 * | 12/2009 | Zucherman et al. .......... 606/267 |
| 7,641,673 B2 | 1/2010 | Le Couedic |
| 7,658,739 B2 | 2/2010 | Shluzas |
| 7,666,189 B2 | 2/2010 | Gerber |
| 7,691,145 B2 | 4/2010 | Reiley |
| 7,699,872 B2 | 4/2010 | Farris |
| 7,749,258 B2 | 7/2010 | Biedermann |
| 7,763,048 B2 | 7/2010 | Fortin |
| 7,763,049 B2 | 7/2010 | Roychowdhury |
| 7,766,944 B2 * | 8/2010 | Metz-Stavenhagen ....... 606/266 |
| 7,776,071 B2 | 8/2010 | Fortin |
| 7,780,706 B2 * | 8/2010 | Marino et al. ................ 606/264 |
| 7,789,897 B2 | 9/2010 | Sanders |
| 7,794,476 B2 | 9/2010 | Wisnewski |
| 7,927,353 B2 | 4/2011 | Taylor |
| 7,976,568 B2 | 7/2011 | Cheung |
| 7,988,713 B2 | 8/2011 | Metz-Stavenhagen |
| 8,002,806 B2 | 8/2011 | Justis |
| 8,007,520 B2 | 8/2011 | Metz-Stavenhagen |
| 8,021,389 B2 | 9/2011 | Molz, IV |
| 8,048,127 B2 | 11/2011 | Moulin |
| 8,048,133 B2 | 11/2011 | Biedermann |
| 8,075,591 B2 | 12/2011 | Ludwig |
| 2001/0020169 A1 | 9/2001 | Metz-Stavenhagen |
| 2002/0032442 A1 | 3/2002 | Altarac |
| 2002/0035366 A1 | 3/2002 | Walder |
| 2002/0082599 A1 | 6/2002 | Crandall |
| 2002/0133155 A1 | 9/2002 | Ferree |
| 2002/0138077 A1 | 9/2002 | Ferree |
| 2002/0143327 A1 | 10/2002 | Shluzas |
| 2002/0143341 A1 | 10/2002 | Biedermann |
| 2002/0169449 A1 | 11/2002 | Kuslich |
| 2002/0173789 A1 | 11/2002 | Howland |
| 2003/0004512 A1 | 1/2003 | Farris |
| 2003/0023240 A1 | 1/2003 | Amrein |
| 2003/0073995 A1 | 4/2003 | Reed |
| 2003/0083657 A1 | 5/2003 | Drewry |
| 2003/0088248 A1 | 5/2003 | Reed |
| 2003/0100896 A1 | 5/2003 | Biedermann |
| 2003/0105460 A1 | 6/2003 | Crandall |
| 2003/0109880 A1 | 6/2003 | Shirado |
| 2003/0114853 A1 | 6/2003 | Burgess |
| 2003/0171749 A1 | 9/2003 | Le Couedic |
| 2003/0176861 A1 | 9/2003 | Reed |
| 2003/0191470 A1 | 10/2003 | Ritland |
| 2003/0203488 A1 | 10/2003 | Mehtali |
| 2003/0220642 A1 | 11/2003 | Freudiger |
| 2003/0220643 A1 | 11/2003 | Ferree |
| 2004/0002708 A1 | 1/2004 | Ritland |
| 2004/0049189 A1 | 3/2004 | Le Couedic |
| 2004/0049190 A1 | 3/2004 | Biedermann |
| 2004/0073215 A1 | 4/2004 | Carli |
| 2004/0106921 A1 | 6/2004 | Cheung |
| 2004/0158258 A1 | 8/2004 | Bonati |
| 2004/0162558 A1 | 8/2004 | Hegde |
| 2004/0172020 A1 | 9/2004 | Beaurain |
| 2004/0172025 A1 | 9/2004 | Drewry |
| 2004/0181224 A1 | 9/2004 | Biedermann |
| 2004/0186472 A1 | 9/2004 | Lewis |
| 2004/0186473 A1 | 9/2004 | Cournoyer |
| 2004/0204711 A1 | 10/2004 | Jackson |
| 2004/0215191 A1 | 10/2004 | Kitchen |
| 2004/0225289 A1 | 11/2004 | Biedermann |
| 2004/0236330 A1 * | 11/2004 | Purcell et al. .................. 606/61 |
| 2004/0254577 A1 | 12/2004 | Delecrin |
| 2004/0260285 A1 | 12/2004 | Steib |
| 2004/0267260 A1 | 12/2004 | Mack |
| 2004/0267275 A1 | 12/2004 | Cournoyer |
| 2005/0010216 A1 | 1/2005 | Gradel |
| 2005/0010233 A1 | 1/2005 | Wittenstein |
| 2005/0010778 A1 | 1/2005 | Walmsley |
| 2005/0033291 A1 | 2/2005 | Ebara |
| 2005/0033295 A1 | 2/2005 | Wisnewski |
| 2005/0038430 A1 | 2/2005 | McKinley |
| 2005/0065514 A1 | 3/2005 | Studer |
| 2005/0065515 A1 | 3/2005 | Jahng |
| 2005/0065516 A1 | 3/2005 | Jahng |
| 2005/0070899 A1 | 3/2005 | Doubler |
| 2005/0070917 A1 | 3/2005 | Justis |
| 2005/0085815 A1 | 4/2005 | Harms |
| 2005/0107788 A1 | 5/2005 | Beaurain |
| 2005/0124991 A1 | 6/2005 | Jahng |
| 2005/0131408 A1 | 6/2005 | Sicvol |
| 2005/0131422 A1 | 6/2005 | Anderson |
| 2005/0149020 A1 | 7/2005 | Jahng |
| 2005/0154390 A1 | 7/2005 | Biedermann |
| 2005/0159650 A1 | 7/2005 | Raymond |
| 2005/0171538 A1 | 8/2005 | Sgier |
| 2005/0177157 A1 | 8/2005 | Jahng |
| 2005/0192573 A1 | 9/2005 | Abdelgany |
| 2005/0192589 A1 | 9/2005 | Raymond |
| 2005/0203511 A1 | 9/2005 | Wilson-MacDonald |
| 2005/0203518 A1 | 9/2005 | Biedermann |
| 2005/0222570 A1 | 10/2005 | Jackson |
| 2005/0222683 A1 | 10/2005 | Berry |
| 2005/0228376 A1 | 10/2005 | Boomer |
| 2005/0228378 A1 | 10/2005 | Kalfas |
| 2005/0228379 A1 * | 10/2005 | Jackson .................... 606/61 |
| 2005/0240265 A1 | 10/2005 | Kuiper |
| 2005/0245928 A1 | 11/2005 | Colleran |
| 2005/0261687 A1 | 11/2005 | Garamszegi |
| 2005/0261770 A1 | 11/2005 | Kuiper |

| | | | | | | |
|---|---|---|---|---|---|---|
| 2005/0277932 | A1 | 12/2005 | Farris | EP | 846444 | 6/1998 |
| 2005/0283244 | A1 | 12/2005 | Gordon | EP | 669109 | 5/1999 |
| 2005/0288668 | A1 | 12/2005 | Brinkhaus | EP | 381588 | 5/2000 |
| 2006/0009767 | A1 | 1/2006 | Kiester | EP | 1295566 | 3/2003 |
| 2006/0015527 | A1 | 1/2006 | Dingle | EP | 880344 | 8/2003 |
| 2006/0025769 | A1 | 2/2006 | Dick | FR | 2624720 | 6/1989 |
| 2006/0036255 | A1 | 2/2006 | Pond | FR | 2786088 | 5/2000 |
| 2006/0064090 | A1 | 3/2006 | Park | FR | 2813782 | 3/2002 |
| 2006/0111715 | A1* | 5/2006 | Jackson ............................ 606/61 | FR | 2839880 | 11/2003 |
| 2006/0149228 | A1 | 7/2006 | Schlapfer | WO | WO 90002527 | 3/1990 |
| 2006/0149236 | A1 | 7/2006 | Barry | WO | WO 9900065 | 1/1999 |
| 2006/0149237 | A1 | 7/2006 | Markworth | WO | WO 99044527 | 9/1999 |
| 2006/0149240 | A1* | 7/2006 | Jackson ............................ 606/61 | WO | WO 0157801 | 12/2001 |
| 2006/0155277 | A1* | 7/2006 | Metz-Stavenhagen ......... 606/61 | WO | WO 0191656 | 5/2002 |
| 2006/0161152 | A1* | 7/2006 | Ensign et al. ..................... 606/61 | WO | WO 02034310 | 2/2003 |
| 2006/0173454 | A1 | 8/2006 | Spitler | WO | WO 2004041100 | 5/2004 |
| 2006/0184171 | A1 | 8/2006 | Biedermann | WO | 2004019755 | 7/2004 |
| 2006/0195092 | A1 | 8/2006 | Barry | WO | WO 2007045899 | 4/2007 |
| 2006/0200129 | A1 | 9/2006 | Denti | WO | WO 2006130179 | 10/2007 |
| 2006/0200131 | A1 | 9/2006 | Chao | WO | WO 2008000944 | 5/2008 |
| 2006/0200132 | A1 | 9/2006 | Chao | | | |
| 2006/0206114 | A1 | 9/2006 | Ensign | | | |
| 2006/0217735 | A1 | 9/2006 | MacDonald | | | |
| 2006/0229607 | A1 | 10/2006 | Brumfield | | | |
| 2006/0229614 | A1 | 10/2006 | Foley | | | |
| 2006/0229615 | A1 | 10/2006 | Abdou | | | |
| 2006/0235389 | A1 | 10/2006 | Albert | | | |
| 2006/0240533 | A1 | 10/2006 | Sengupta | | | |
| 2006/0264935 | A1 | 11/2006 | White | | | |
| 2006/0264937 | A1 | 11/2006 | White | | | |
| 2006/0271193 | A1 | 11/2006 | Hartmann | | | |
| 2006/0282073 | A1 | 12/2006 | Simanovsky | | | |
| 2007/0016201 | A1 | 1/2007 | Freudiger | | | |
| 2007/0049937 | A1 | 3/2007 | Matthis | | | |
| 2007/0055240 | A1* | 3/2007 | Matthis et al. ................... 606/61 | | | |
| 2007/0090238 | A1* | 4/2007 | Justis ........................ 248/181.1 | | | |
| 2007/0161990 | A1 | 7/2007 | Hillyard | | | |
| 2007/0161994 | A1 | 7/2007 | Lowery | | | |
| 2007/0162007 | A1 | 7/2007 | Shoham | | | |
| 2007/0162009 | A1 | 7/2007 | Chao | | | |
| 2007/0162010 | A1 | 7/2007 | Chao | | | |
| 2007/0173800 | A1 | 7/2007 | Sanders | | | |
| 2007/0173828 | A1 | 7/2007 | Firkins | | | |
| 2007/0179501 | A1 | 8/2007 | Firkins | | | |
| 2007/0191831 | A1 | 8/2007 | Sanders | | | |
| 2007/0191841 | A1 | 8/2007 | Justis | | | |
| 2007/0191842 | A1 | 8/2007 | Molz | | | |
| 2007/0198088 | A1 | 8/2007 | Biedermann | | | |
| 2007/0213721 | A1 | 9/2007 | Markworth | | | |
| 2007/0213723 | A1 | 9/2007 | Markworth | | | |
| 2007/0239154 | A1 | 10/2007 | Shaolian | | | |
| 2007/0270843 | A1 | 11/2007 | Matthis | | | |
| 2007/0288013 | A1 | 12/2007 | Sanders | | | |
| 2008/0021456 | A1 | 1/2008 | Gupta | | | |
| 2008/0027436 | A1 | 1/2008 | Cournoyer | | | |
| 2008/0058805 | A1 | 3/2008 | Stuart | | | |
| 2008/0071373 | A1 | 3/2008 | Molz | | | |
| 2008/0114404 | A1 | 5/2008 | Matthis | | | |
| 2008/0195159 | A1* | 8/2008 | Kloss et al. ..................... 606/305 | | | |
| 2008/0234756 | A1 | 9/2008 | Sutcliffe | | | |
| 2008/0243189 | A1 | 10/2008 | Purcell | | | |
| 2008/0269805 | A1 | 10/2008 | Dekutoski | | | |
| 2009/0048632 | A1 | 2/2009 | Firkins | | | |
| 2009/0182381 | A1 | 7/2009 | Beaurain | | | |
| 2009/0198280 | A1 | 8/2009 | Spratt | | | |
| 2009/0222042 | A1 | 9/2009 | Firkins | | | |
| 2010/0010547 | A1 | 1/2010 | Beaurain | | | |
| 2010/0042156 | A1 | 2/2010 | Harms | | | |
| 2010/0063548 | A1 | 3/2010 | Wang | | | |
| 2010/0114169 | A1 | 5/2010 | Le Couedic | | | |
| 2010/0114173 | A1 | 5/2010 | Le Couedic | | | |
| 2010/0249848 | A1 | 9/2010 | Wisnewski | | | |

FOREIGN PATENT DOCUMENTS

| | | |
|---|---|---|
| EP | 134622 | 10/1986 |
| EP | 592266 | 4/1994 |
| EP | 470660 | 7/1995 |
| EP | 558883 | 7/1997 |
| EP | 811357 | 12/1997 |

OTHER PUBLICATIONS

Andreasen G (1980) A clinical trial of alignment of teeth using 0.019-inch thermal nitinol wire with transitional temperature range between 31°C and 45°C. Am Orthod 78:528-537.

Asher MA, Burton DC. Adolescent idiopathic scoliosis: natural history and long term treatment effects. Scoliosis 2006; 1:2.

Betz Rr, Kim J, D'Andrea LP, et al. An innovative technique of vertebral body stapling for the treatment of patients with adolescent idiopathic scoliosis: a feasibility, safety, and utility study. Spine 2003;28(suppl):255-65.

Bischoff R, Bennett Jt, Stuecker R, et al. The use of TexasScottish-Rite instrumentation in idiopathic scoliosis. A preliminary report. Spine 1993 18:2452-2456.

Boos N, Webb Jk. Pedicle screw fixation in spinal disorders : A European view. Eur Spine) 1997;6:2-18.

Braun et al., "Mechanical modulation of vertebral growth in the fusion less treatment of progressive scoliosis in an experimental model"; Spine; 2006 May 20; 31(12):1314-20.

Braun JT, Hines JL, Akyuz E Relative versus absolute modulation of growth in the fusionless treatment of experimental scoliosis. Spine 2006, 15;31:1776-82.

Braun JT, Ogilvie JW, Akyuz E, et al. Fusionless scoliosis correction using a shape memory alloy staple in the anterior thoracic spine of the immature goat. Spine 2004;29: 1980-9.

Bridwell KH. Surgical treatment of idiopathic adolescent scoliosis. Spine 1999;24:2607-16.

Brymill Cryogenic Systems, "CRY-AC & CRY-AC-3," retrieved online at: http://www.brymill.com/catalog_1_cryac.htm (2010).

Chemtronics Technical Data Sheet, "Freez-lt Freeze Spray," TDS#1550E Date Unknown.

Cotrel Y, Dubousset, Guillaumat M. New universal instrumentation in spinal surgery. Clin Orthop 1988;227: 10-23.

Cryosurgery, Inc, "Verruca-Freeze is a convenient and effective cryosurgical system for the treatment of benign skin lesions," retrieved online at: http://www.cryosurgeryinc.com/cryo/cryosurgeryweb. nsf/0/9C997EB18781696E85256DCB005627D2?opendocument (2005).

Cryosurgery, Inc., "Comparison of Cryosurgical Systems," Date Unknown.

GHS Medical, "Our Light Coagulator Product Family," retrieved online at: http://www/ghs-medical.com/geraeteha02.htm (2005).

Goshi K, Boachie-Adjei 0, Moore C, Nishiyama M. Thoracic scoliosis fusion in adolescent and adult idiopathic scoliosis using posterior translational corrective techniques (Isola): is maximum correction of the thoracic curve detrimental to the unfused lumbar curve? Spine J 2004; 4:192-201.

Halm HF, Niemeyer T, Link TM, et al. Segmental pedicle screw instrumentation in idiopathic thoracolumbar and lumbar scoliosis. Eur Spine) 2000; 9:192-7.

Hamill Ci, Lenke IG, Bridwell KH, et al. The use of pedicle screw fixation to improve correction in the lumbar spine of patients with idiopathic scoliosis. Is it warranted? Spine 1996;21: 1241-9.

Harrington PRo Treatment of scoliosis: correction and internal fixation by spine instrumentation. J Bone Joint Surg Am 1962;44:591634.

Kim YJ, Lenke LG, Kim J, et al. Comparative analysis of pedicle screw versus hybrid instrumentation in posterior spinal fusion of adolescent idiopathic scoliosis. Spine 2006;31:291-298.

Lehman Ra Jr, Polly Dw Jr, Kuklo TR, et al. Straight-forward versus anatomic trajectory technique of thoracic pedicle screw fixation: A biomechanical analysis. Spine 2003; 28:2058-2065.

Liljenqvist UR, Halm HF, Link TM. Pedicle screw instrumentation of the thoracic spine in idiopathic scoliosis. Spine 1997;22:2239-45.

Liu Xm, Wu Si, Chan YL, et al. Surface characteristics, biocompatibility, and mechanical properties of nickel-titanium plasma-implanted with nitrogen at different implantation voltages.J Biomed Mater Res A. 2007; 82:469-78.

Lumatec "Infrared-Coagulator" Date Unknown.

Matsumoto K, Tajima N, Kuwahara S. Correction of scoliosis with shape-memory alloy.Nippon Seikeigeka Gakkai Zasshi. 1993 Apr;67(4): 267-74.

Misenhimer GR, Peek Rd, Wiltse LL, et al. Anatomic analysis of pedicle cortical and cancellous diameter as related to screw size. Spine 1989;14:367-72.

NDC, Nitinol Devices & Components, "Nitinol Technology," retrieved online at: http://www.nitinol.com/3tech.htm (2001).

Niti Smart Sheet, retrieved online at: http://www.sma.inc.com (2001).

Puttlitz et al,. A biomechanical assessment of thoracic spine stapling. Spine. 2007 Apr.

Sanders, "Preliminary investigation of shape memory alloys in the surgical correction of Scoliosis"; Spine; Sep. 15, 1993; 18(12):1640-6.

Steinmann JC, Herkowitz HN, el-Kommos H, et al. Spinal pedicle fixation: Confirmation of an image-based technique for screw placement. Spine 1993; 18:8560-61.

Suk Si, Kim W), lee Sm, Kim )H, Chung ER. Thoracic pedicle screw fixation in spinal deformities: are they really safe? Spine 2001;26:2049-57.

Suk Si, lee Ck, Kim W), et al. Segmental pedicle screw fixation in the treatment of thoracic idiopathic scoliosis. Spine 1995;20: 1399-405.

Svetlana A., Shabaloskay A. Surface corrosion and biocompatibility aspects of Nitinol as an implant material, Journal of Biomedical Materials Engineering, 2002, 12: 692109.

Szold A. Nitinol: shape-memory and super-elastic materials in surgery. *Surg Eiidosc*. 2006;20:1493-1496, doi: 10,1007/s00464-005-0867-1.

Takeshita K, Maruyama T, Murakami M, et al. Correction of scoliosis using segmental pedicle screw instrumentation versus hybrid constructs with hooks and screws. Stud Health Technol Inform 2006; 123:571-576.

Veldhuizen, a.G. et al., "A scoliosis correction device based on memory metal," Med. Eng. Phys., vol. 19 (2):171-179 (1997).

Wang a, Peng ), Zhang X, et al.Experimental study of recovery force of surface-modified TiNi memory alloy rod Sheng Wu Yi Xue Gong Cheng Xue Za Zhi. 2006;23:774-7.

Wever et al., "Scoliosis correction with shape-memory metal: results of an experimental study"; .Eur Spine J.; Apr. 2002; 11(2):100-6. Epub Nov. 14, 2001.

Wu S, Liu X, Chan Yl,et al.Nickel release behavior, cytocompatibility, and superelasticity of oxidized porous single-phase NiTLJ Biomed Mater Res A. 2007; 81 :948-55.

Yeung KW, Poon RW, Chu Pk,et al.Surface mechanical properties, corrosion resistance, and cytocompatibility of nitrogen plasma-implanted nickel-titanium alloys: a comparative study with commonly used medical grade materials.) Biomed Mater Res A. 2007; 82:403-14.

Zdeblick'Anterior Spinal Fixation after Lumbar Corpectomy'A Study in Dogs, Journal of Bone and Joint Surgery, vol. 73-A, #4, Apr. 1991, p. 527-537.

Zindrick MR, Knight GW, Satori MJ, et al. Pedicle morphology of the immature thoracolumbar spine. Spine 2000;25:2726-35.

Denkhausa K, Salnikow B. Nickel essentiality, toxicity, carcinogenicity [J ]. Critical Reviews Oncology/Hematology, 2002, 42, pp. 352-56.

Wiltse, Leon L. et al., "History of Pedicle Screw Fixation of the Spine," Spine, State of the Art Reviews, vol. 6(1):1-10 (1992).

* cited by examiner

ASSEMBLY FOR ORTHOPAEDIC SURGERY

BACKGROUND

The present invention relates to a bone screw, a clamp for clamping the bone screw to a support element and an assembly of the clamp and bone screw. The present invention is for use in orthopedic surgery and particularly spinal surgery.

Surgical procedures are known in which a support element is fixed to the vertebrae in order to hold the vertebrae in a fixed position relative to each other and cause fusion of the spine. A variety of assemblies for connecting a vertebra to a support element for use in these methods of surgery are known. One family of devices are referred to as polyaxial screws. These devices generally comprise a bone screw which is inserted into a clamping element. The bone screw has a head portion with a convex surface that engages a corresponding concave surface within the clamping element. Relative movement between these two surfaces allows the angle of the axis of the screw to be moved relative to the axis of the clamp.

As a further development of these devices, screws which can be rotated within a single plane relative to a clamp have also been proposed. One such screw is discussed in EP-A-1774919. This describes a fixation element, or screw, which can be pivoted in a single plane relative to a receiving part. The movement of the screw in a single plane is limited by a pressure element. The pressure element engages the head of the screw to limit its movement. The head of the screw is formed from two opposite spherical surfaces joined by two cylindrically shaped surfaces. The interaction of the surfaces with the pressure element limit the screw to pivotal movement in a single plane.

US-A-2006/0155277 also relates to a screw that can be rotated within a single plane. An anchoring element, or screw, has a head comprising two flat guiding surfaces. The head is retained within an intermediate element which has corresponding counter surfaces to limit the head to rotate within a single plane.

A surgeon can select an appropriate type of screw depending on the range of relative movement required between the screw and the clamp. For example, depending on the situation in which the support element is required to be attached to a vertebrae, the surgeon may opt for a polyaxial screw which can be pivoted about several planes relative to a clamp, or a uniplanar screw, for example, as discussed in EP-A-1774919 or US-A-2006/0155277. In some circumstances, the surgeon may wish to use a screw which cannot be moved relative to the clamp. Thus, there is a requirement for a large inventory of suitable assemblies for fixing a support element to the vertebrae.

The majority of known polyaxial screw assemblies, including those described in EP-A-1774919 and US-A-2006/0155277, are also required to be assembled with the screw located in the clamp before the screw is inserted into a bone. This can cause difficulties when screwing the screw into the bone, particularly if the clamp is angled relative to the axis of the screw because in that case the clamp would need to rotate with the screw and will sweep out a cone as the screw is screwed in.

A clamp for a polyaxial screw is proposed in US-A-2003/0023240. The clamp can be inserted onto a spherical head of a polyaxial screw after the screw has been inserted into the bone. The clamp engages the spherical head by the use of a collet chuck comprising spring loaded tongues. The tongues can be deformed outwards to enable insertion or removal of a spherical head bone screw into the bottom of the clamp. However, this device cannot be adapted for use with screws other than polyaxial screws that can rotate relative to the clamp in several planes. It also presents a disadvantage because an axial force is required to be applied to both insert and remove the screw. This axial force may be required to be considerable to ensure that the spherical head is located securely in the clamp.

U.S. Pat. No. 6,716,214 relates to a polyaxial bone screw with spline capture connection. The polyaxial bone screw includes a bone implantable shank, a head and a retaining ring. The shank includes a capture structure with at least one spline with a wedged surface for engaging the retaining ring. In normal use the shank, head and retaining ring are assembled before the structure is screwed into the bone. In certain circumstances the shank can first be implanted before the capture structure engages the retaining ring. The use of wedge shaped splines means that subsequent disassembly is difficult.

WO-A-2004/041100 discusses a spinal stabilisation system using polyaxial bone fastener assemblies. The system includes bone fasteners with one or splines that engage a ring which is then inserted into a collar to provide polyaxial movement between the ring and the collar in a similar way to U.S. Pat. No. 6,716,214.

SUMMARY

Accordingly, the present invention provides a bone screw having a head with two parallel substantially planar sides. A curved surface joins the planar sides. A head of this design can engage a variety of inserts that, together with a clamp, allows a degree of freedom of movement of the screw relative to the clamp to be controlled. In addition, the combination of parallel substantially flat sides joined by a curved surface enables the head of the present invention to be inserted into a clamp after it has been installed in the bone, and then locked securely in the clamp by a relative rotation between the clamp and the head of the screw. This provides the bone screw of the present invention with more flexibility for insertion, and possible subsequent revision, than systems such as those in U.S. Pat. No. 6,716,214 and WO-A-2004/041100 which use splines.

According to a first aspect of the present invention, there is provided an assembly for connecting a support element to a bone comprising:
  a bone screw having a head at one end of a threaded shaft; and
  a clamp comprising:
    a base at a first end of the clamp delimiting an opening for receiving the head of the bone screw; and
    at least two side members extending from the base towards a second end of the clamp;
    wherein the head of the bone screw and the clamp are configured to allow the head of the bone screw to be inserted into the base from the direction of the first end at a first orientation of the base to the bone screw, and to retain an inserted bone screw within the base at a second orientation of the base relative to the bone screw.

The assembly allows the screw to be inserted into a clamp after it has been installed in the bone. The configuration of the head and the opening allows this to happen without requiring any significant axial pressure; the screw can be locked within a clamp simply by a relative rotation of the clamp and the screw. This provides a further advantage of allowing subsequent revision surgery to be carried out easily, without requiring removal of the screw from the bone. If it were not possible to remove the clamp from the screw after it had been installed in the body, as with the device of EP-A-1774919, it would only be possible to revise the system using the original clamp attached to the screw without requiring removal of the screw from the bone. Similar problems are encounter with the spline based systems of U.S. Pat. No. 6,716,214 and WO-A-2004/041100. With an assembly according to the present invention, the screw can remain in the body, and a clamp can be removed and replaced with an alternative clamp. This allows revision of the system without requiring removal of the screw from a bone, while allowing a surgeon to alter the degree of freedom of the screw to move relative to the clamp during the revision.

In one embodiment, the head of the bone screw comprises:
two substantially planar surfaces generally opposite each other and parallel to each other; and
a curved surface that extends between at least a part of the substantially planar surfaces and is curved at least in a plane parallel to the substantially planar surfaces;
wherein the greatest dimension of the head portion, in a direction parallel to the at substantially planar surfaces, is greater than the distance between the two substantially planar surfaces.

The configuration of the head allows the screw to be constrained by a variety of inserts that engage the head in different ways to limit its freedom of movement relative to a clamp, reducing the inventory required.

Preferably, the two substantially planar surfaces are parallel to the longitudinal axis. This enables the screw to be inserted easily into a clamp without requiring any complicated orientation of the screw relative to a clamp.

The curved surface may define a portion of a cylindrical surface. Preferably the axis of the cylinder is perpendicular with the longitudinal axis and passes through the longitudinal axis. In use, the cylindrical surface can form a bearing surface for the screw to pivot around the axis of the cylinder.

Alternatively, the curved surface may define a portion of a spherical surface. Preferably, the centre of the spherical surface lies on the longitudinal axis. The portion of the spherical surface can then form a bearing surface allowing the screw to rotate in several planes if required.

The head may comprise an edge or apex at the furthest point from the threaded shaft in a direction of the longitudinal axis. The edge or apex may be defined by two surfaces meeting at an angle in a plane perpendicular to the substantially planar surfaces. The edge or apex provides a protrusion which an insert can engage in order to limit pivotal movement of the screw if required.

In one embodiment, the point of the head furthest from the threaded shaft in the direction of the longitudinal axis comprises an apex which is on the longitudinal axis. In an alternative embodiment, the point of the head of the screw furthest from the threaded shaft in the direction of the longitudinal axis may comprise an edge which intersects the longitudinal axis. The edge may be parallel with the substantially planar surfaces. In both of these embodiments, the edge or the apex may form a point about which the head of the screw can pivot relative to an insert.

In one embodiment, the base delimits an opening having a central axis and the second orientation is a rotation of the clamp about the central axis. Preferably, the rotation is approximately 90°. This allows the head of the bone screw to be inserted into the clamp without requiring an axial force and retained simply by a relative rotation of the clamp, again requiring no axial force.

The opening may be delimited by an edge at the first end of the base and an at least partially concave surface may extend from the edge towards the second end. The concave surface can interact with the curved surface of the head of the screw to allow pivotal movement of the screw within the clamp. The at least partially concave surface may be cylindrical or, more preferably, spherical as this allows a greater degree of potential movement of the screw relative to the clamp.

In one embodiment, the head of the screw has a maximum perimeter in a plane perpendicular to the longitudinal axis and wherein the opening is delimited by an edge at the first end of the base that defines a perimeter at least corresponding to the maximum perimeter in a first orientation of the head to the central axis, and a perimeter smaller in at least one dimension than the maximum perimeter in a second orientation of the head to the central axis.

The assembly may further comprise an insert member for insertion between the at least two side members and configured to engage the head of the bone screw and to control the freedom of the bone screw to move relative to the clamp.

By providing an insert member, the freedom of the bone screw to move relative to the clamp is controlled. This reduces inventory and allows a surgeon to select the appropriate freedom of movement after the bone screw has been installed in a bone. This also facilitates subsequent revision surgery when it is desired to alter the freedom of movement of the screw. The freedom of movement can then simply be altered by changing the insert member, without needing to remove the screw from the bone.

In one embodiment, the insert member is configured to engage the head of the bone screw such that the bone screw can rotate relative to the insert member about an axis perpendicular to the plane of the substantially planar surfaces of the head of the bone screw. For example, the insert member comprises two screw bearing surfaces, which are substantially planar and parallel to each other for engaging the substantially planar surfaces of the head of the bone screw. In this case, the interaction between the two substantially planar surfaces ensures that the screw can pivot relative to the clamp only in a single plane. The two screw bearing surfaces can be angled with respect to the central axis of the opening or parallel with respect to the central axis of the opening. This allows the angle of the plane in which the screw pivots to be altered, depending on surgical requirements.

In an alternative embodiment, the insert member is configured to engage the head of the bone screw such that the bone screw cannot move relative to the insert member. In this embodiment, the screw is fixed relative to the clamp and cannot be pivoted relative to it. For example, the insert member may comprise two surfaces meeting at an angle of less than 180° that engage the head of the bone screw. For example, if the head of the bone screw comprises an edge or apex, the two surfaces meeting at an angle in the insert member can be configured to engage the edge or apex and ensure that no relative movement between the insert member and the screw can occur.

In another embodiment, the insert member may have an at least partially convex spherical outer surface. Thus, the insert head can provide additional convex surface for the screw, enabling the screw to pivot in more than one plane. For example the convex spherical outer surface may be configured to cover the substantially planar surfaces of the head of the screw, thereby essentially forming spherical head for the screw.

The insert member may comprise a surface for at least partially receiving a support element. Alternatively, the assembly may further comprise a shoulder member for insertion between the at least two side members, the shoulder member comprising having a first surface for abutting the insert member and a second surface for at least partially receiving a support element.

The shoulder member can provide benefits by adapting the surface of the insert member to secure the interface with the support element. For example, if the support element has a circular cross-section, the shoulder member could have a concave cylindrical surface for receiving the support element. Likewise, if the support element has a square or rectangular cross-section, the shoulder member can define a generally U-shaped cross-section with a flat bottom for receiving the support element. Thus, the shoulder member allows the assembly to be adapted to receive support elements of a variety of different cross-sections, further reducing the inventory required.

In one embodiment the first surface of the shoulder member abuts the insert member to define a bearing surface allowing relative movement of the insert member to the shoulder member. The bearing surface could be flat or alternatively could be at least partially concave, depending on the required freedom of movement of the screw. For example, if the insert member has an at least partially convex spherical outer surface, a corresponding concave spherical surface could be provided on the shoulder member. Alternatively, the bearing surface could be flat or substantially planar simply allowing the insert member to rotate relative to the shoulder member.

The assembly may further comprise a securing element for securing a support element in the clamp. Preferably, at least a portion of the side members comprises grooved defining a screw thread and the securing element is a set screw for engaging the screw threads.

The securing element can be configured to exert a force onto the support element. It can then press the support element against the insert member (and shoulder member if one is included) transferring a pressure force onto the head of the screw. This forces the head of the screw against the sides of the opening, creating a friction force to lock the screw at a particular orientation relative to the clamp.

According to a still further aspect of the present invention, there is provided a system for spinal surgery comprising at least two assemblies as described above and a support element for fixing to the at least two assemblies. Thus, the support element can be fixed to two vertebrae and hold them in a fixed position relative to each other.

According a yet further aspect of the present invention, there is provided a system for securing a support element to a bone, comprising:
 a bone screw having a head at one end of a threaded shaft; and
 a clamp comprising:
  a base at a first end of the clamp delimiting an opening for receiving the head of the bone screw; and
  at least two side members extending from the base towards a second end of the clamp; and
 at least two insert members for insertion between the at least two side members wherein each of the insert members is configured to engage the head of the bone screw in a different way to control the freedom of the bone screw to move relative to the clamp.

Such a system provides an assembly that can be used when the surgeon requires a polyaxial screw, uniplanar screw or fixed screw simply choosing an appropriate insert member. This has the benefit of reducing inventory. The more detailed features of the bone screw, clamp and insert members described above may also be applied to this aspect.

The present invention can be used in a method of surgery comprising:
 implanting a bone screw into a vertebra of a patient,
 inserting a head of the implanted bone screw into the base of a clamp delimiting an opening with a central axis at a first orientation to the central axis;
 rotating the clamp relative to the central axis of the bone screw to a second orientation relative to the longitudinal axis, such that the bone screw is retained within the clamp;
 inserting a support element into the clamp; and
 securing the support element in the clamp.

The second orientation may be rotated by 90° relative to the first orientation. The method can also include, before the insertion of the head portion into the clamp, selecting an insert member and placing it in the clamp, wherein the insert member is configured to engage the head of the bone screw and to control the freedom of the bone screw to move relative to the clamp.

DESCRIPTION OF THE DRAWINGS

Embodiments of the description will now be described by way of example with reference to the accompanying drawings, in which.

Like reference numerals are used throughout the drawings and description to indicate like parts.

DETAILED DESCRIPTION

Figure 1:
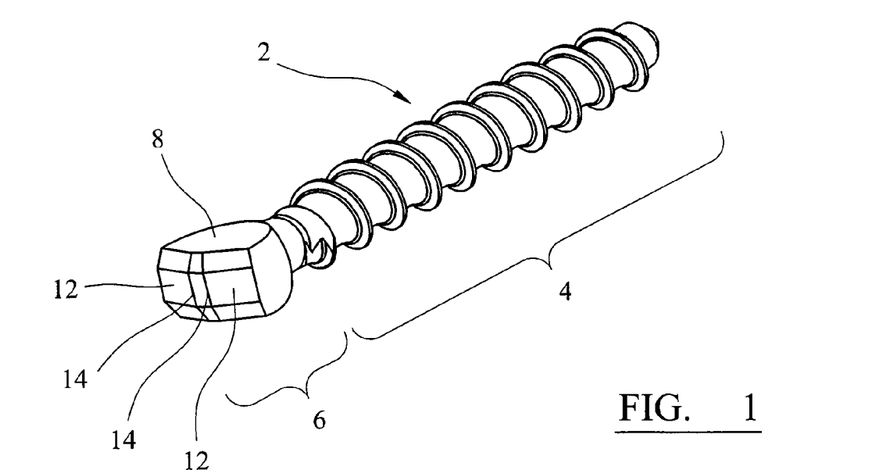
FIG. 1 depicts a perspective view of a bone screw according to a first aspect of the present invention.

FIG. 1 depicts a perspective view of a screw 2 according to a first embodiment of the present invention. The screw 2 comprises a threaded shaft 4 and a head 6. The head 6 comprises two parallel, opposite planar surfaces 8 joined by a curved surfaces 10. The curved surface 10 is curved both in the plane parallel to the planar surface 8 and in a plane perpendicular to the curved surface 8. At the end of the head 6, a number of angled surfaces 12 are provided the surfaces meet defining edges 14 at the part of the head 6 furthest from the threaded shaft 4.

Figure 2:
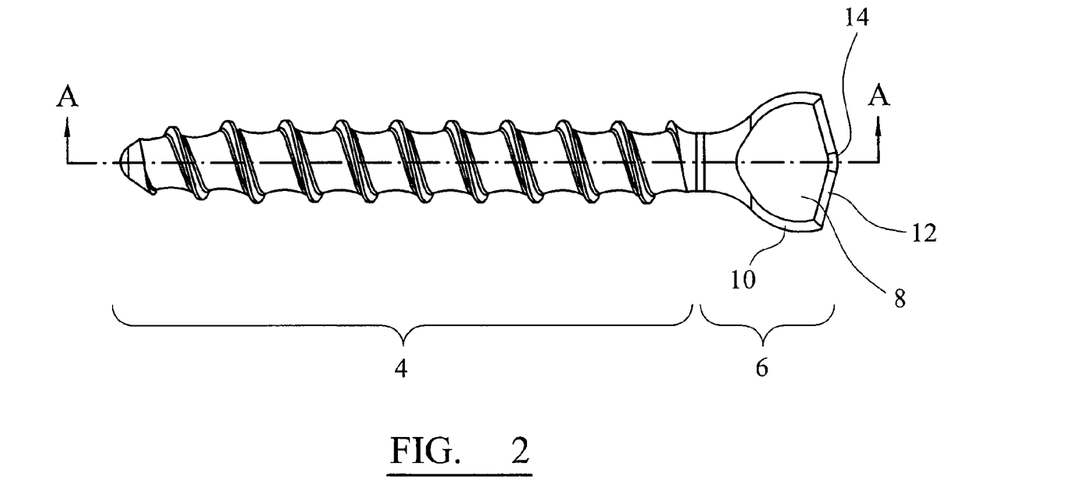
FIG. 2 depicts a top view of the screw of FIG. 1.
Figure 3:
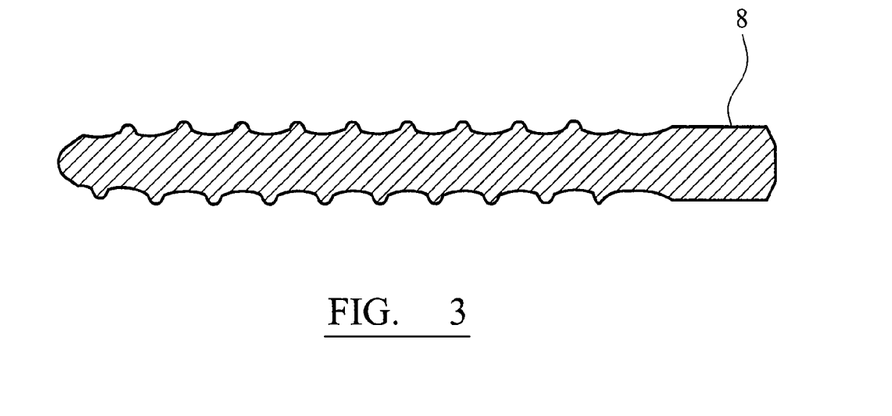
FIG. 3 depicts a cross-section of the screw of FIG. 1 along line A-A in FIG. 2.

A top view of the screw of FIG. 1, looking directly at the planar surface 8, is depicted in FIG. 2. This shows how the curved surface 10 is curved in a plane parallel to the planar surface 8, which can clearly be seen by the curve visible in the drawing. A cross-section of the screw along line A-A in FIG. 2 is depicted in FIG. 3. This shows how the surfaces 8 are planar. It also illustrates how the distance between the planar surfaces 8 is less than the greatest distance between the curved surfaces 10, as can be seen depicted in FIG. 2. The greatest distance between the curved surfaces 10, in a plane parallel to the planar surfaces 8, is greater than the distance between the planar surfaces 8.

Figure 4:
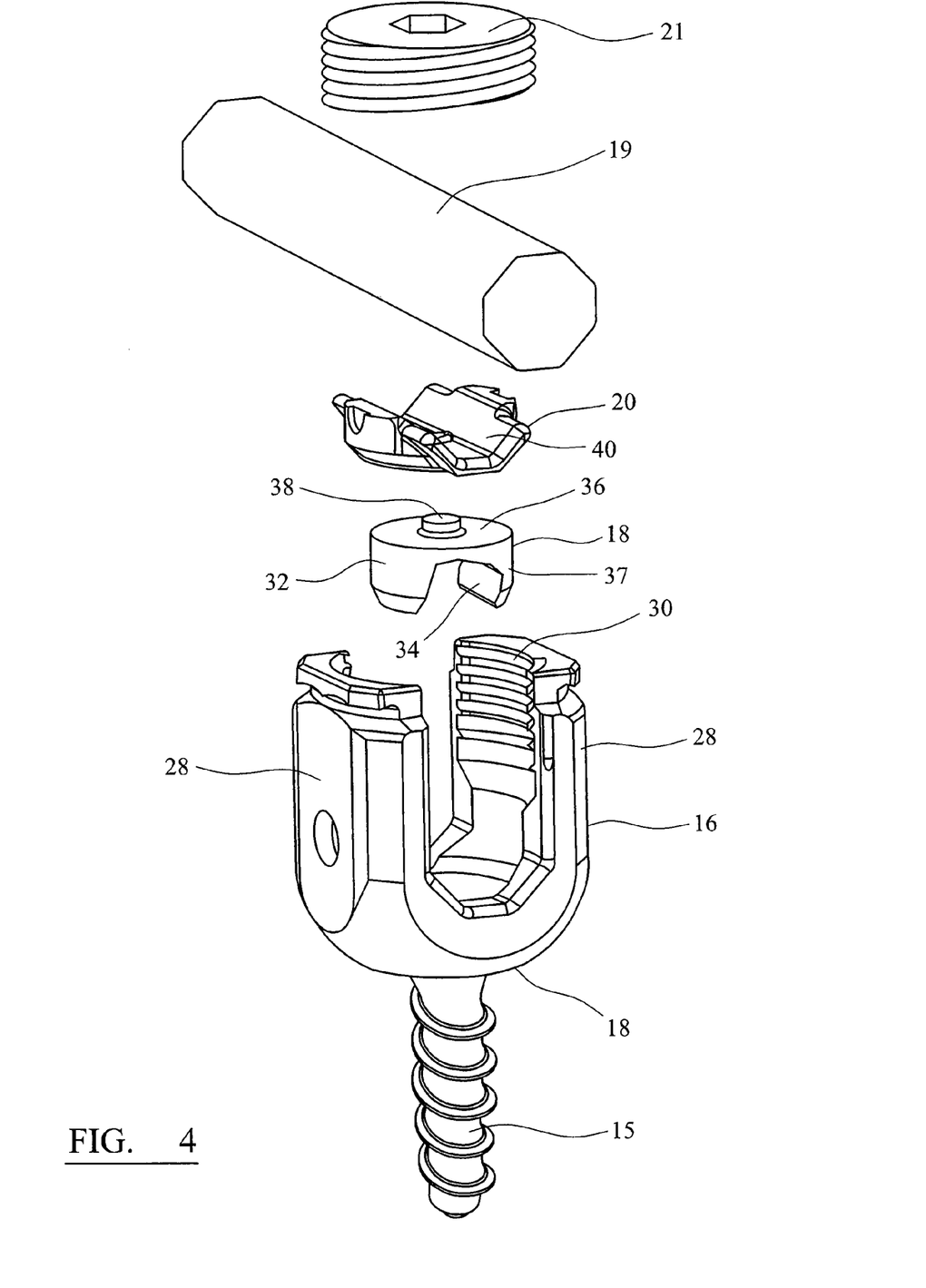
FIG. 4 depicts an exploded view of a partial assembly according to an embodiment of the present invention.

The screw depicted in FIGS. 1-3 is intended to be used in a clamp assembly. One embodiment of a clamp assembly is depicted in FIG. 4. The assembly comprises a bone screw 15, a clamp 16, an insert member 18, a shoulder member 20, a support element 19 and a set screw 21. The clamp member 16 is depicted viewed from the bottom direction of FIG. 4, looking up through the base.

Figure 5:
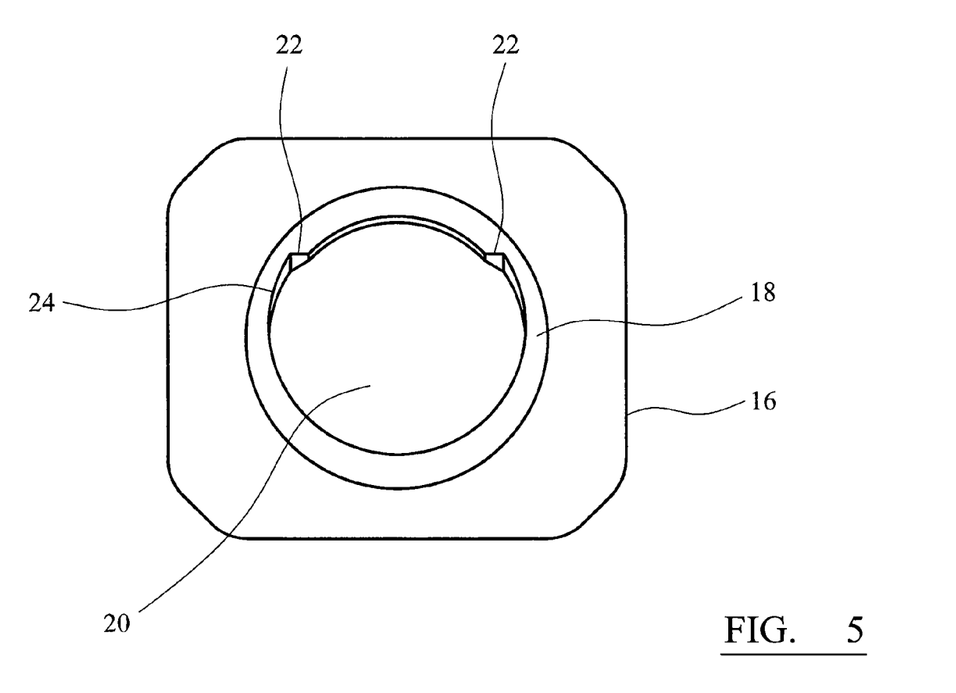
FIG. 5 depicts a plan view of an embodiment of a clamp according to the present invention, viewed from bottom surface.
Figure 6:
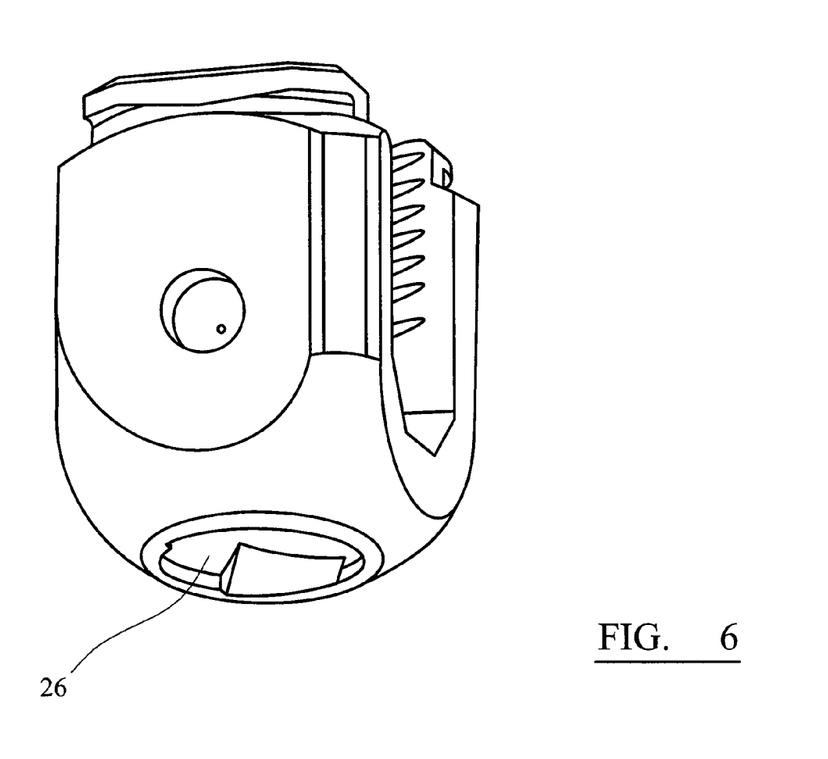
FIG. 6 depicts a perspective view of the clamp depicted in FIG. 5.

A perspective view of the clamp 16 as seen from the direction of the base of the clamp is depicted in FIG. 6. As can be seen most clearly in FIG. 5, the base 18 of the clamp 16 comprises an edge which has an opening 20. The opening 20 is sized to enable the head 6 of the screw 2 to be inserted at a first orientation of the head 6 relative to the opening 20. Once inserted into the clamp 16, the clamp 16 can then be rotated relative to the head 6 of the screw 2 in order to retain the screw 2 within the clamp 16. In order to achieve this, the perimeter of the opening 20 in this embodiment includes two protrusions 22. The protrusions 22 act to either allow the head 6 of the screw 2 to be inserted, or to retain the head 6 within the clamp 16, depending on the relative orientation of the head 6 to the clamp 16.

Considering FIG. 5, it can be seen that the protrusions 22 each comprise a planar surface. This allows the head 6 to be inserted when the planar surfaces 8 are aligned with the planar surface of the protrusions 22. Once inserted into the clamp 16, the head of the clamp can then be rotated through 90°, whereupon the planar surfaces 8 of the head 6 are then located perpendicularly to the plane of the protrusions 22, and the protrusions 22 act to retain the head 6 within the clamp 16.

In order to ensure that the head 6 can be received easily, and is guided into the correct position within the opening 20, the surface of the clamp 16 within the opening 20 includes an angled portion 24. In addition to this angled portion 24, the remainder of the internal surface of the clamp 16 extending from the opening 20 has a concave curve. This curved surface is indicated generally at 26 in FIG. 6. The concave curved surface 26 can engage the curved surface 10 on the head 6 of the screw 2.

Referring back to FIG. 4, the clamp 16 can be seen to comprise a base 18 and two side members 28 extending generally perpendicularly to the base. The far end of the side members 28 comprises a series of grooves 30 which define a screw thread for receiving a set screw 21. FIG. 4 also depicts an insert member 18. In this embodiment, the insert member 18 is intended to restrict the movement of the screw 2 to pivoting within a single plane, which is angled with respect to a central axis of the opening 20. To achieve this, the insert member 18 includes two side members 32 extending downwardly, each having angled planar surfaces 34 opposite each other. The angle of the planar surfaces 34 determines the angle of the plane in which the screw 2 can pivot. An upper surface 36 of the insert member 18 is substantially planar and comprises a protrusion 38 at its centre.

The protrusion 38 engages a corresponding recess in the shoulder member 20. The shoulder member 20 also comprises a corresponding planar surface to enable the insert member 18 to rotate relative to the shoulder member 20, rotating about the axis of the protrusion 38.

This embodiment is intended for use with a support element having a generally octagonal cross-section. The shoulder member 20 therefore includes a surface 40 that is angled corresponding to the angles of the support element so that the support element is abutted on three sides by the shoulder member 20.

Figure 7:
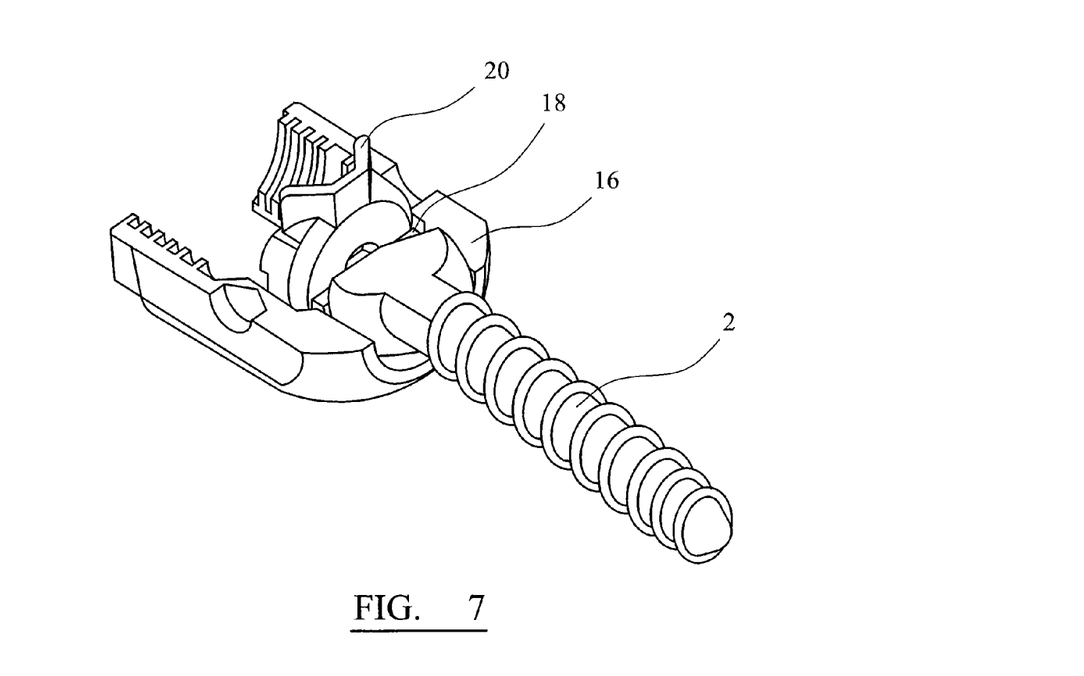
FIG. 7 depicts a partially cut-away perspective view of an assembly according to an embodiment of the present invention at a first orientation.
Figure 8:
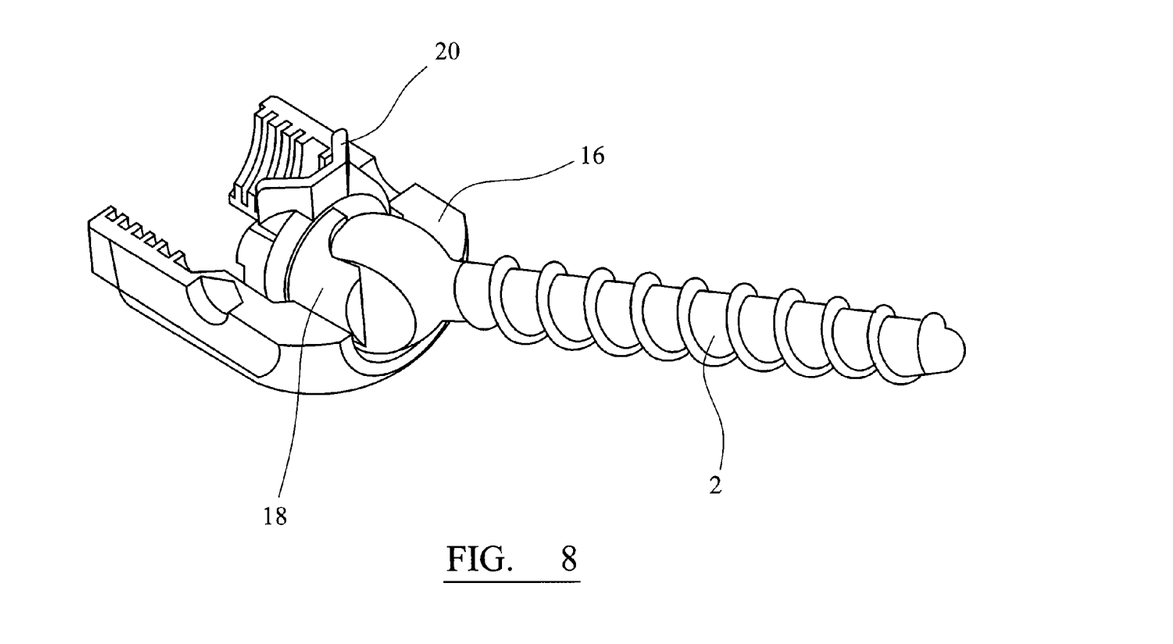
FIG. 8 depicts a partially cut-away perspective view of the embodiment of FIG. 7 in a second orientation.

A partially cut-away perspective view of an assembly of the screw 2, clamp 16, insert member 18 and shoulder member 20 is depicted in FIG. 7 in a first orientation and FIG. 8 in a second orientation. FIG. 7 depicts the orientation in which the screw can be inserted into the opening 20 in the base of the clamp 16. In this configuration the planar surfaces 8 of the screw are aligned with the planar surfaces 34 of the shoulder member 18 (not visible in FIG. 7). The protrusion 38 can be seen engaging the recess in the shoulder member 20. The shoulder member 20 and the two side members 28 of the clamp 16 can be seen to define a channel for receiving the support element.

FIG. 8 depicts the assembly of FIG. 7 in a second orientation in which the head 6 of the screw 2 is retained within the clamp 16. In order to retain the screw 2 within the clamp 16, the clamp 16 and shoulder member 20 are rotated relative to the screw 4 and insert member 18. (In FIG. 8, for greater clarity this relative movement has been depicted as a movement of the screw 16 and insert member 18.) As can readily be seen by comparing FIG. 7 and FIG. 8, the relative position of the shoulder member 20 and the clamp 16 do not change. However, the screw 2 and the insert member 18 rotate within the clamp 16. In the position illustrated in FIG. 8, the curved surface 10 of the screw 2 can engage a corresponding curved surface formed within the clamp 16. This enables the screw 2 to pivot in a single plane, with the planar surface of the screw 8 forming a bearing surface with the planar surface 34 of the insert member 18. FIG. 8 also clearly shows the angling of the planar surface 34 of the insert member 18 in this embodiment.

The components of this embodiment are preferably manufactured from titanium but any other bio-compatible material could also be used in alternate embodiments, including metals, metal alloys (for example stainless steel and cobalt chrome), polymers and composites.

Figure 9:
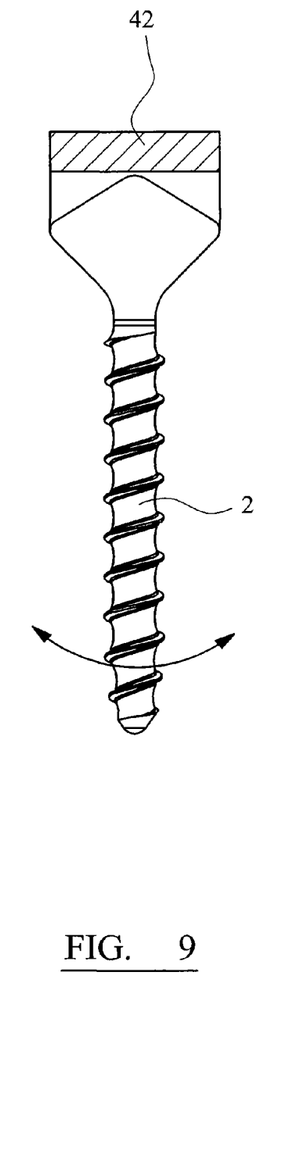
FIG. 9 is a diagrammatic representation of a screw and insert member according to another embodiment of the invention.
Figure 10:
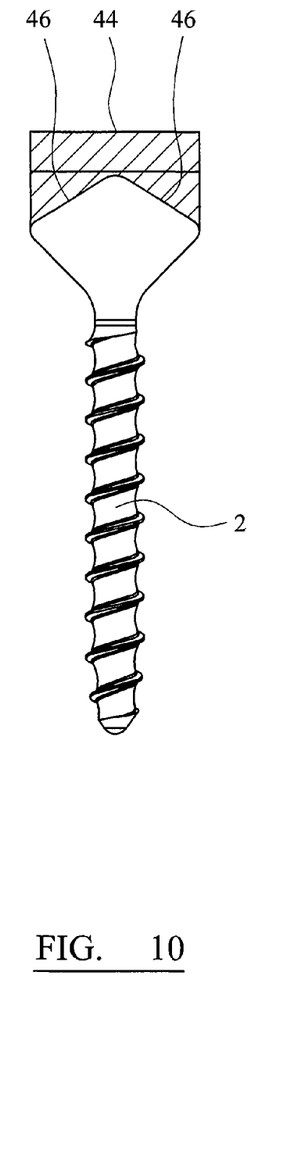
FIG. 10 is a diagrammatic representation of a screw and insert member according to a further embodiment of the invention.
Figure 11:
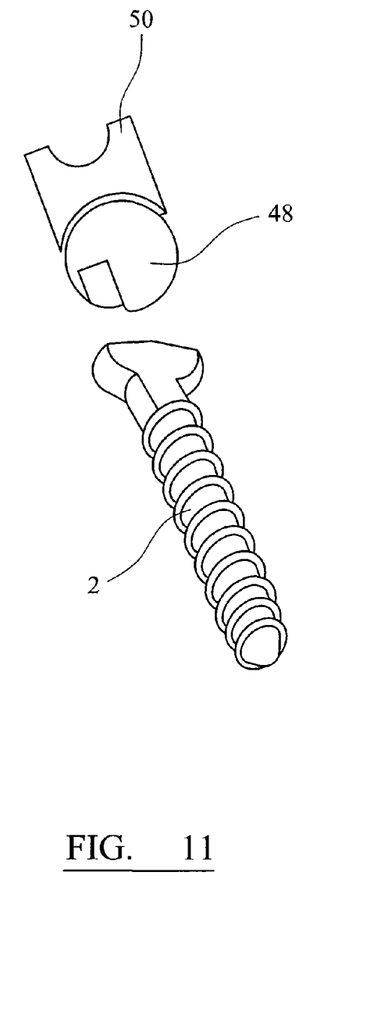
FIG. 11 is a diagrammatic representation of a screw, insert member and shoulder member according to a still further embodiment of the present invention.

The assembly described above is only one embodiment that can be used with the screw 2 of the present invention. A variety of different insert members can be provided depending on the degree of freedom with which the screw 2 is desired to move within the clamp 16. FIGS. 9, 10 and 11 are diagrammatic representations of alternative embodiments in which the freedom of the screw 2 to move is different from the above described embodiment.

FIG. 9 depicts an alternative embodiment in which the screw 2 is also constrained to move within a single plane. However, in this case, the shoulder member 42 includes two planar surfaces which are not angled. This means that the screw is limited to pivoting in a plane which is parallel to the central axis of the opening, rather than angled with respect to the central axis of the opening.

FIG. 10 depicts an embodiment of an insert member 44 which prohibits movement of the screw relative to the insert member or clamp. It can be seen that the insert member 44 comprises two surfaces 46 that meet at an angle of less than 180°. The two surfaces engage the corresponding surfaces formed on the head of the screw 2 to grip the head of the screw 2 and prevent its movement relative to the insert member 44.

An additional alternate embodiment is depicted in FIG. 11. In this embodiment the screw 2 is configured to pivot about multiple planes relative to the central axis of the opening of the clamp. In order to achieve this the insert member 48 takes a different form from the previous embodiment. The insert member 48 has a spherically convex surface and combines with the existing convex curved surface on the head of the screw 2 to define a substantially spherical surface. This spherical surface interacts with a corresponding concave spherical surface formed on the shoulder member 50. In this embodiment the shoulder member 50 could be a standard shoulder used with existing polyaxial screws as known to the person skilled in the art. As depicted in FIG. 11 the shoulder member 50 is intended for use with support elements having a circular cross-section and therefore includes a semi-circular recess on its upper surface.

Figures 12, 13:
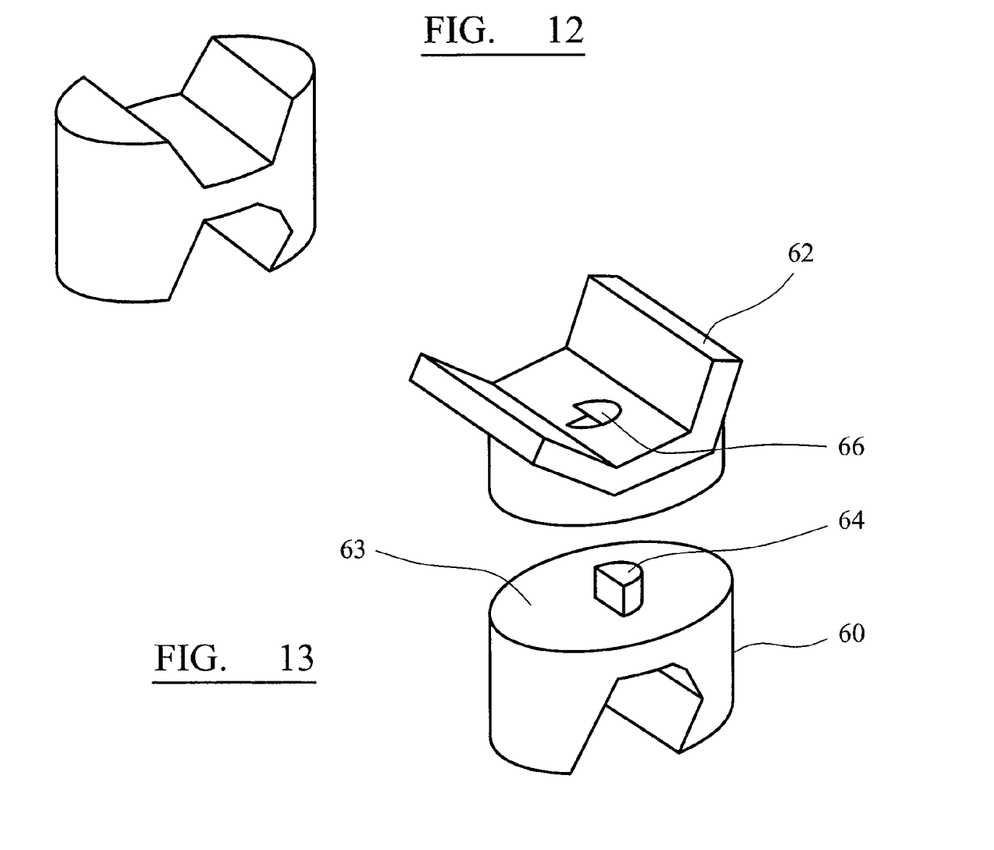
FIG. 12 is a diagrammatic representation of a combined insert and shoulder member used in an alternate embodiment of the present invention.
FIG. 13 is a diagrammatic representation of a insert and shoulder member including a rotational stop.

In alternate embodiments the shoulder member and insert member may be combined into a single component. An example of such a combine shoulder and insert member is depicted in FIG. 12.

In another alternate embodiment, the rotational connection between the shoulder member and the insert member can be configured to allow only limited rotation between the insert member and the shoulder member. FIG. 13 depicts an example of the shoulder and insert members including a rotation stop. They are illustrated without the other parts of the assembly for clarity. An insert member 60 engages a shoulder member 62. A semi-circular protrusion 64 extends from a bearing surface 63 of the shoulder member 60. A corresponding recess 66 is formed in shoulder member 62. The recess 66 is in the form of a segment of a circle. In this embodiment the segment extends over an angle of 270°.

Figure 13A:
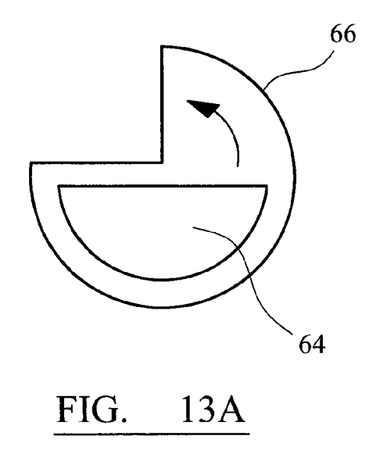
Figure 13B:
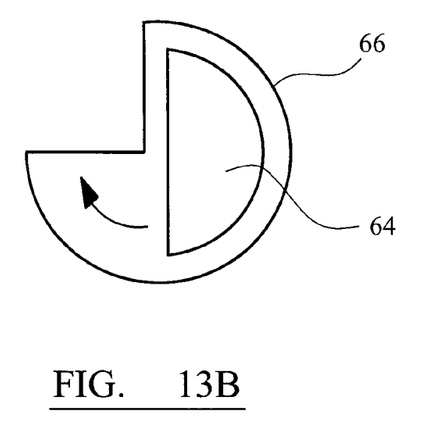

FIGS. 13A and 13B illustrate the interaction between the protrusion 64 and the recess 66 that creates the rotational stop. The segment of the recess is 90° greater than the angle of 180° over which the semi-circular protrusion extends. The insert member can therefore be rotated by 90° relative to the shoulder member 62 to allow locking of the screw in the opening, between a first position depicted in FIG. 13A and a second position depicted in FIG. 13B. Alternative angular dimensions may be used in alternate embodiments.

In still further alternate embodiments (not illustrated) the bearing surfaces where relative rotation takes place can be provided with small protrusions, nodes or bumps which extend from each surface. These can act to increase friction between the components and also provide tactile feedback to a surgeon during relative movement of components. For example the components may "click" as they move past each other.

It will be appreciated that many variations of the above described embodiments can fall within the scope of the present invention. In particular, the present invention may be used with support elements of any cross-sectional shape. The configuration of the head portion may also be varied from those specific examples given. The key feature of the head portion is a pair of planar surfaces joined by a curved surface. The opening of the base of the clamp may also be configured differently, depending on the specific way in which the head portion is configured, providing that the head portion can be inserted into the opening in a first orientation and locked in the opening in a second orientation.

The present invention provides many advantages over existing polyaxial screw systems. A single bone screw can be adapted to have varying degrees of freedom relative to a clamp depending on the requirements of the surgeon. This can vary between a full polyaxial screw that can pivot about several planes relative to an axis of an opening, a screw limited to pivoting in a single plane, or a screw which cannot move relative to the clamp. The configuration of the head of the screw also enables it to be inserted and removed from a clamp once the screw has been inserted into the bone, without needing to remove the screw from the bone. This simplifies the surgical procedure, as there is no need to negotiate the clamp while screwing in the screw and provides a benefit of easier revision.

The screw and assembly of the present invention can be used in a method of surgery in which the screw is installed into the bone before being installed in the clamp. The installation of the screw into the clamp involves simply inserting the head of the screw at a first orientation and then rotating the screw relative to the clamp in order to lock it within the clamp. This avoids the application of axial forces to screw. The present invention also allows revision surgery where the clamp and insert member can be changed if necessary without requiring to remove the screw from the bone.

We claim:

1. An assembly for connecting a support element to a bone, the assembly comprising:
    a bone screw having a head at one end of a threaded shaft, the head having substantially planar surfaces;
    a clamp comprising:
        a base at a first end of the clamp delimiting an opening for receiving the head of the bone screw; and
        at least two side members extending from the base towards a second end of the clamp;
    an insert member for insertion between the at least two side members and configured to engage the head of the bone screw such that the bone screw can rotate relative to the insert member only about an axis perpendicular to a plane defined by the substantially planar surfaces of the head of the bone screw; and
    a shoulder member for insertion between the at least two side members, the shoulder member having a first surface for abutting the insert member and a second surface for at least partially receiving a support element, the first surface of the shoulder member abutting the insert member to define a bearing surface allowing relative movement of the insert member to the shoulder member;
    wherein the head of the bone screw and the clamp are configured to allow the head of the bone screw to be inserted into the base from the direction of the first end at a first orientation of the base to the bone screw, and to retain an inserted bone screw within the base at a second orientation of the base relative to the bone screw.

2. An assembly according to claim 1, wherein the head of the bone screw comprises:
    two substantially planar surfaces generally opposite each other and parallel to each other; and
    a curved surface that extends between at least a part of the substantially planar surfaces and is curved at least in a plane parallel to the substantially planar surfaces;
    wherein the greatest dimension of the head, in a direction parallel to the substantially planar surfaces, is greater than the distance between the two substantially planar surfaces.

3. An assembly according to claim 1, wherein the threaded shaft has a longitudinal axis and the head of the bone screw comprises an edge or apex at the furthest point from the threaded shaft in the direction of the longitudinal axis.

4. An assembly according to claim 1, wherein the opening has a central axis and the second orientation is a rotation of the clamp about the central axis.

5. An assembly according to claim 1, wherein the opening is delimited by an edge at the first end of the base and an at least partially concave surface extends from the edge towards the second end.

6. An assembly according to claim 1, wherein the head of the screw has a maximum perimeter in a plane perpendicular to a longitudinal axis of the screw and wherein the opening is delimited by an edge at the first end of the base that defines a perimeter at least corresponding to the maximum perimeter in a first orientation of the head to a central axis of the opening, and a perimeter smaller in at least one dimension than the maximum perimeter in a second orientation of the head to the central axis.

7. An assembly according to claim 1, wherein the insert member comprises two screw bearing surfaces, which are substantially planar and parallel to each other for engaging the substantially planar surfaces of the head of the bone screw.

8. An assembly according to claim 7, wherein the two screw bearing surfaces are angled with respect to the central axis of the opening.

9. An assembly according claim 1, further comprising a securing element for securing a support element in the clamp.

10. An assembly according to claim 9, wherein at least a portion of the side members comprises a grooved defining a screw thread and the securing element is a set screw for engaging the screw thread.

11. A assembly according to claim 1, wherein the insert member is rotatable relative to the shoulder member.

12. A system for spinal surgery comprising:
  at least two assemblies, wherein each assembly comprises:
    a bone screw having a head at one end of a threaded shaft, the head having substantially planar surfaces;
    a clamp comprising:
      a base at a first end of the clamp delimiting an opening for receiving the head of the bone screw; and
      at least two side members extending from the base towards a second end of the clamp;
    an insert member for insertion between the at least two side members and configured to engage the head of the bone screw such that the bone screw can rotate relative to the insert member about an only axis perpendicular a plane defined by the substantially planar surfaces of the head of the bone screw; and
    a shoulder member for insertion between the at least two side members, the shoulder member having a first surface for abutting the insert member and a second surface for at least partially receiving a support element;
    wherein the head of the bone screw and the clamp are configured to allow the head of the bone screw to be inserted into the base from the direction of the first end at a first orientation of the base to the bone screw, and to retain an inserted bone screw within the base at a second orientation of the base relative to the bone screw; and
  a support element for fixing to the at least two assemblies.

13. A system according to claim 12, wherein the first surface of the shoulder member abuts the insert member to define a bearing surface allowing relative movement of the insert member to the shoulder member.

14. A system according to claim 13, wherein the insert member is rotatable relative to the shoulder member.

* * * * *